United States Patent [19]

Carter et al.

[11] Patent Number: 5,607,917
[45] Date of Patent: Mar. 4, 1997

[54] METHODS FOR REDUCING BLOOD LOSS

[75] Inventors: Bruce L. A. Carter, Mercer Island; Martin W. Edwards, Woodinville, both of Wash.

[73] Assignee: ZymoGenetics, Inc., Seattle, Wash.

[21] Appl. No.: 456,018

[22] Filed: May 31, 1995

Related U.S. Application Data

[63] Continuation of Ser. No. 291,315, Aug. 17, 1994, abandoned, which is a continuation of Ser. No. 815,443, Dec. 31, 1991, abandoned.

[51] Int. Cl.$^6$ .......................... A61K 38/00; A61K 38/16; C07K 2/00; C07K 4/00
[52] U.S. Cl. ................................ 514/12; 530/381; 514/2; 514/8
[58] Field of Search ................................ 530/381; 514/12

[56] References Cited

U.S. PATENT DOCUMENTS

| | | |
|---|---|---|
| 4,235,877 | 11/1980 | Fullerton . |
| 4,311,712 | 1/1982 | Evans et al. . |
| 4,370,349 | 1/1983 | Evans et al. . |
| 4,464,355 | 8/1984 | Fabricius et al. . |
| 4,518,584 | 5/1985 | Mark et al. . |
| 4,522,811 | 6/1985 | Eppstein et al. . |
| 4,565,696 | 1/1986 | Heath et al. . |
| 4,599,227 | 7/1986 | Dees et al. . |
| 4,604,377 | 8/1986 | Fernandes et al. . |
| 4,636,463 | 1/1987 | Altman et al. . |
| 4,663,161 | 5/1987 | Mannino et al. . |
| 4,683,199 | 7/1987 | Palladino . |
| 4,684,625 | 8/1987 | Eppstein et al. . |
| 4,689,222 | 8/1987 | McMichael . |
| 4,690,915 | 9/1987 | Rosenberg . |
| 4,721,612 | 1/1988 | Janoff et al. . |
| 4,752,425 | 6/1988 | Martin et al. . |
| 4,774,085 | 9/1988 | Fidler . |
| 4,781,871 | 11/1988 | West, III et al. . |
| 4,808,151 | 2/1989 | Dunn, Jr. et al. . |
| 5,017,556 | 5/1991 | O'Brien et al. .................. 530/381 |
| 5,047,406 | 9/1991 | Lobernour et al. .............. 530/381 |

FOREIGN PATENT DOCUMENTS

| | | |
|---|---|---|
| 902089 | 10/1985 | Belgium . |
| 49611 | 4/1982 | European Pat. Off. . |
| 172007 | 2/1986 | European Pat. Off. . |
| 178624 | 4/1986 | European Pat. Off. . |
| 203403 | 12/1986 | European Pat. Off. . |
| 225130 | 5/1987 | European Pat. Off. . |
| 240346 | 9/1987 | European Pat. Off. . |
| 274219 | 6/1988 | European Pat. Off. . |
| 62-30708 | 2/1987 | Japan . |
| 2157172 | 10/1985 | United Kingdom . |
| WO85/00515 | 2/1985 | WIPO . |
| WO85/00751 | 2/1985 | WIPO . |
| WO85/03640 | 8/1985 | WIPO . |
| WO85/03948 | 9/1985 | WIPO . |
| WO87/04592 | 9/1987 | WIPO . |
| WO88/00970 | 2/1988 | WIPO . |
| WO89/05149 | 6/1989 | WIPO . |
| WO89/05657 | 6/1989 | WIPO . |
| WO89/05631 | 6/1989 | WIPO . |
| WO89/09831 | 10/1989 | WIPO . |
| WO89/11270 | 11/1989 | WIPO . |

OTHER PUBLICATIONS

Bohrer et al. "Adverse hemodynamic Effects . . . Surgical Patient", 1990.
Egbring et al., Fibrinogen 3, Biochemistry, biological functions, gene regulation and expression:341–346, 1988.
Mishima et al., Chirurg 55: 803–808, 1984.
Baer et al., Zbl. Chirurgie 105: 642–651, 1980.
Shainoff et al., The XI Int. Fibrinogen Workshop, Oslo, Norway, Jun. 24–26, 1992.
Williams et al., eds., Hematology, Fourth Ed., McGraw Hill Publishing Co., at pp. 1775–1776 1978; 1982; 1986.
Coln et al., Am. J. Surg. 145: 256–259, 1983.
Francis and Marder, Blood 71: 1363–1365, 1988.
Francis and Marder, J. Clin. Invest. 80: 1459–1465, 1987.
P. M. Anderson et al., Cancer Immunol. Immunother., 1988, 27, 82.
P. M. Anderson et al., J. Biol. Chem., 1979, 254, 6924.
P. M. Anderson et al., J. Immunol., 1989, 142, 1383.
P. M. Anderson et al., Proceed. Amer. Assoc. Cancer Res., 1989, 30, 364.
P. M. Anderson et al., Abstract of paper presented at FASEB, New Orleans, Mar. 1989.
P. M. Anderson et al., J. Cell. Biochemistry, 1988, 12, Part B, 255, Abstract W100.
N. Berinstein et al., J. Immunol., 1988, 140, 2839.
C. G. Brooks et al., J. Immunol., 1985, 135, 1145.
M. J. Brunda et al., Int. J. Cancer, 1986, 37, 787.
D. J. A. Crommelin et al., Pharm. Res., 1984, 1, 159.
H.–A. Fabricius et al., Immunobiol., 1979, 156, 364.
R. I. Fisher et al., Ann. Int. Med., 1988, 108, 518.
E. A. Forssen et al., Cancer Res., 1983, 43, 546.
J. H. Frenster et al., in Proc. 5th Leukocyte Culture Conference, J. E. Harris, ed. (1970), p. 359.
C. J. Froelich et al., J. Immunol. Meth., 1986, 86, 205.
J. Fujita, Eur. J. Cancer Clin. Oncol., 1986, 22, 445.
S. Gillis et al., J. Immunol., 1978, 120, 2027.
M. F. Good et al., J. Immunol., 1988, 141, 972.
R. E. Gordon et al., Drug Dev. Ind. Pharm., 1982, 8, 465.
G. Gregoriadis and A. C. Allison, eds., Liposomes in Biological Systems, John Wiley & Sons, New York (1980), at pp. 153–178.
E. A. Grimm et al., J. Exp. Med., 1983, 158, 1356.
E. A. Grimm et al., J. Exp. Med., 1983, 157, 884.
H. H. Hsieh et al., Transplantation Proceedings, 1985, XVII, 1397.
K. J. Hwang, in Liposomes from Biophysics to Therapeutics, M. J. Ospro, ed., Marcel Decker, New York (1987) at pp. 109–156.

(List continued on next page.)

Primary Examiner—Elizabeth C. Weimar
Assistant Examiner—Phynn Touzeau
Attorney, Agent, or Firm—Gary E. Parker

[57] ABSTRACT

Blood loss in a patient undergoing surgery, particularly thoracic or abdominal surgery, is reduced by administration of factor XIII. The factor XIII may be administered in combination with aprotinin.

12 Claims, No Drawings

OTHER PUBLICATIONS

K. Itoh et al., *J. Immunol.*, 1985, 134, 3124.
K. Itoh et al., *J. Immunol.*, 1986, 136, 3910.
E. M. Janis et al., *Science*, 1989, 244, 713.
M. Kende et al., *Antimicrobial Agents and Chemotherapy*, 1985, 27, 903.
H. Konno et al., *Chemical Abstracts*, 1989, 110, No. 19, 624, Abstract No. 171523s.
S. S. Kulkarni et al., *Annals of the New York Academy of Sciences*, 1987, 507, 344.
O. Leo et al., *Proc. Natl. Acad. Sci. USA*, 1987, 84, 1374.
G. Lopez–Berestein, *Ann. Int. Med.*, 1986, 105, 130.
M. Malkovsky et al., *Nature*, 1987, 325, 262.
S. C. Meuer et al., *Proc. Natl. Acad. Sci. USA*, 1984, 81, 1509.
S. Miescher et al., *J. Immunol.*, 1986, 136, 1899.
J. J. Mule et al., *Science*, 1984, 225, 1487.
L. M. Muul et al., *J. Immunol.*, 1987, 138, 989.
L. M. Muul et al., *J. Immunol. Meth.*, 1986, 88, 26.
J. H. Nunberg et al., *J. Cell. Biochem.*, 1988, Supp. 128, 12.
A. C. Ochoa et al., *Cancer Res.*, 1989, 49, 963.
A. C. Ochoa et al., *J. Immunol.*, 1987, 138, 2728.
J. R. Ortaldo et al., *Int. J. Cancer*, 1983, 31, 285.
G. Poste et al., *Cancer Research*, 1979, 39, 881.
M. J. Poznansky and R. L. Juliano, *Pharmacol. Rev.*, 1984, 36, 277.
H. Rabinowich et al., *Cancer Res.*, 1987, 47, 173.
A. Rahman et al., *Cancer Res.*, 1982, 42, 1817.
S. A. Rosenberg, in *Important Advances in Oncology*, V. T. DeVita et al., eds., J. P. Lippincott Co., Philadelphia, Pennsylvania (1988) at pp. 217 to 257.
S. A. Rosenberg et al., *J. Immunol*, 1978, 121, 1951.
S. A. Rosenberg et al., *Adv. Cancer Res.*, 1977, 25, 323.
S. A. Rosenberg et al., *Ann. Int. Med.*, 1988, 108, 853.
S. A. Rosenberg et al., *Ann. of Surg.*, 1988, 208, 121.
S. A. Rosenberg et al., *N. Engl. J. Med.*, 1985, 313, 1485.
S. A. Rosenberg et al., *N. Engl. J. Med.*, 1987, 316, 889.
S. A. Rosenberg et al., *Science*, 1986, 233, 1318.
D. G. Russell et al., *J. Immunol.*, 1988, 140, 1274.
B. E. Ryman et al., *Essays in Biochemistry*, 1980, 16, 49.
R. R. Salup et al., *Cancer Immunol. Immunother.*, 1986, 22, 31.
R. Schwab et al., *J. Immunol.*, 1985, 135, 1714.
S. Shu et al., *J. Immunol.*, 1986, 136, 3891.
S. Shu et al., *J. Immunol.*, 1985, 135, 2895.
K. A. Smith, *Science*, 1988, 240, 1169.
S. Sone et al., *Cell Immunol.*, 1981, 57, 42.
S. Sone et al., *J. Immunol.*, 1980, 125, 2454.
G. Strauss et al., *Proc. Natl. Acad. Sci. USA*, 1986, 83, 2422.
G. Strauss et al., *Biochem. Biophys. Acta*, 1986, 858, 169.
J. L. Strausser et al., *J. Immunol.*, 1978, 121, 1491.
A. B. Stavitsky, *J. Immunol.*, 1954, 72, 360.
L. Tan et al., *Biochemical Society Transactions*, 1989, 17, 693.
V. von Fliedner et al., *Progress in Chemical and Biological Research: Cellular Immunotherapy of Cancer*, 1987, 244, 223.
B. M. Vose, *Int. J. Cancer*, 1982, 30, 135.
A. Weinberg et al., *J. Immunol.*, 1988, 140, 294.
A. Weiss et al., *J. Clin. Immunol.*, 1984, 4, 165.
T. L. Whiteside et al., *Int. J. Cancer*, 1986, 37, 803.
J. M. Williams et al., *J. Immunol.*, 1985, 135, 2249.
J. M. Zarling et al., *Nature*, 1978, 274, 269.
O. Zumbuehl et al., *Biochem. Biophys. Acta*, 1981, 640, 252.
S. C. Yang et al., *Proc. Annu. Meet. Am. Assoc. Cancer Res.*, 29 (1988), Abstract No. A1603 (Meeting Abstract).
Y. P. Yen et al., *Proc. Annu. Meet. Am. Assoc. Cancer Res.*, 28 (1987), Abstract No. 403 (Meeting Abstract): and Y. P. Yen et al., *Proc. Annu. Meet. Am. Assoc. Cancer Res.*, 29 (1988), Abstract No. A1616 (Meeting Abstract).
J. M. Zarling et al., *Cancer Immunol. Immunother.*, 15, 237 (1983).
T. D. Geppert et al., *J. Clin. Invest.*, 81, 1497 (1988).
E. A. Grimm et al., *J. Exp. Med.*, 155, 1823 (1982).
M. T. Lotze et al., *Cancer Res.*, 41, 4420 (1981).
M. T. Lotze et al., *J. Surg. Res.*, 42, 580 (1987).
E. Lotzova et al., *Nat. Immun. Cell Growth Regul.*, 6, 219 (1987).
G. B. Mills et al., *J. Cell. Physiol.*, 141, 310 (1989).
R. P. Moser et al., *Int'l. Symp. on Pediatric Neuro–Oncology*, Jun. 1–3, 1989, Seattle, WA, Meeting Abstract No. A14.
S. Rosenberg, *J.N.C.I.*, 75, 595 (1985).
P. M. Sondel et al., *J. Immunol.*, 137, 502 (1986).
J. Stankova et al., *FASEB*, 2, (1988) Abstract No. 2114, 72nd Annual Meeting of FASEB, May 1988 (Meeting Abstract).
J. Stankova et al., *Cell. Immunol.*, 121, 13 (1988).
M. C. Turco et al., *Blood*, 74, 1651 (1989).
W. H. West et al., *J. Immunol.*, 118, 355 (1977).

METHODS FOR REDUCING BLOOD LOSS

This is a continuation of application Ser. No. 08/291,315, filed Aug. 17, 1994, now abandoned which is a continuation of application Ser. No. 07/815,443, filed Dec. 31, 1991, now abandoned.

BACKGROUND OF THE INVENTION

Blood loss is a serious complication of open-heart and other major surgeries. Cardiac surgery patients account for a significant proportion of transfused donor blood. Blood transfusion carries risks of disease transmission and adverse reactions. In addition, donor blood is expensive, and demand often exceeds supply.

Pharmacological and other methods for reducing blood loss and the resultant need for transfusion have been described (reviewed by Scott et al., *Ann. Thorac. Surg.* 50: 843–851, 1990). Prostacyclin and desmopressin acetate have been tested, but results with desmopressin acetate have been inconclusive, and neither of these agents has been able to eliminate the need for postoperative transfusion.

Bovine aprotinin has been reported as being effective in reducing perioperative blood loss (Royston et al., *Lancet* ii: 1289–1291, 1987; Dietrich et al., *Thorac. Cardiovasc. Surq.* 37: 92–98, 1989; Fraedrich et al., *Thorac. Cardiovasc. Surg.* 37: 89–91, 1989), but adverse effects, including hypotension and flushing (Bohrer et al., *Anaesthesia* 45: 853–854, 1990) and allergic reaction (Dietrich et al., ibid.) have been reported. The use of aprotinin in patients previously exposed to it is not recommended (Dietrich et al., ibid.). The use of blood-derived aprotinin does not eliminate the risk of transmission of viral diseases. Moreover, aprotinin has not yet been approved for use in the United States.

There remains a need in the art for a reliable and widely applicable method of reducing blood loss during and after surgery. In particular, there is a need for a method that is non-immunogenic and does not rely on blood-derived products. There is also a need for a method that does not produce the adverse side effects seen with aprotinin therapy. The present invention fulfills this need by providing an improved method of reducing perioperative blood loss.

DISCLOSURE OF THE INVENTION

The present invention provides methods for reducing perioperative blood loss in a patient undergoing surgery, wherein an effective amount of factor XIII in a biologically compatible vehicle is administered to the patient. Within one embodiment, the factor XIII is administered to the patient as a bolus injection, typically within one day prior to surgery. Within another embodiment, the factor XIII is administered at a dose of 0.1–1.0 mg per kg of patient weight, preferably 0.15–0.4 mg per kg. Within another embodiment, aprotinin is also administered to the patient.

These and other aspects of the invention will become evident upon reference to the following detailed description.

DETAILED DESCRIPTION OF THE INVENTION

The present invention provides improved methods for reducing perioperative blood loss in patients undergoing surgery, in particular, in patients undergoing major thoracic or abdominal surgery or other surgeries having the potential for loss of large volumes of blood. These methods reduce or eliminate the need for whole donor blood or blood products, thereby reducing the risk of infection and other adverse side effects, as well as the cost of surgery. The methods are thus useful in reducing blood loss in normal patients, i.e. those not suffering from inborn or other pre-operative bleeding disorders such as defects or deficiencies in coagulation factors. The reduction in blood loss is seen as a reduction in blood loss during surgery, as reduced post-surgical drainage, or both.

Within the methods of the present invention, an effective amount of factor XIII is combined with a biologically compatible vehicle and administered to a patient. Suitable vehicles include sterile, non-pyrogenic aqueous diluents, such as sterile water for injection, sterile buffered solutions or sterile saline. The resulting composition is administered to the patient prior to and/or during surgery by intravenous injection or infusion. Within a preferred embodiment, the factor XIII composition is administered as a bolus up to one week prior to surgery, but preferably within one day prior to surgery.

Factor XIII (also known as "fibrinoligase" [Lorand et al., *Prog. Hemost. Thromb.* 5: 245–290, 1980] and "fibrin stabilizing factor [Curtis and Lorand, *Methods Enzymol.* 45: 177–191, 1976]) is characterized by its ability, when activated, to form intermolecular γ-glutamyl-ε-lysine cross links between side chains of fibrin molecules and between other substrates. The enzyme exists in plasma as a tetrameric zymogen of two a subunits and two b subunits (designated $a_2b_2$), but is found in other tissue as an $a_2$ dimer. Either of these zymogen forms, or activated factor XIII (factor XIIIa), may be used within the present invention, as well as genetically engineered variants of factor XIII that retain its characteristic cross-linking activity.

Within the present invention an "effective amount" of factor XIII is defined as that amount sufficient to reduce blood loss during or after surgery by at least 15%. The amount of factor XIII administered will be sufficient to provide a supranormal plasma level of factor XIII. An effective amount of factor XIII will generally be in the range of about 0.1 to 1.0 mg per kg of patient weight, i.e. a dose of about 10 mg to about 70 mg for a 70 kg patient. Doses in the range of about 0.15 mg to 0.4 mg per kg of patient weight are particularly preferred. The actual amount of factor XIII administered will depend in part on such factors as the nature of the surgery and overall patient condition, including pre-existing factor XIII levels. In the event of excessive blood loss during surgery, additional factor XIII may be administered.

Within one embodiment of the invention, factor XIII is administered in combination with aprotinin. Aprotinin (e.g. Trasylol, Bayer AG, Leverkusen, Germany) is administered according to methods known in the art, including intravenous infusion before and during surgery and through the oxygenator. In general, a dose of between about $2 \times 10^6$ KIU and $8 \times 10^6$ KIU will be used, depending on such factors as patient weight and the length of the surgery. Typically, a dose of about $2 \times 10^6$ KIU is provided in the priming volume of the extracorporeal circulation. An additional $2 \times 10^6$ KIU may be provided as a loading dose prior to surgery, together with continuous administration of ca. 500,000 KIU per hour. See Royston et al., ibid., Dietrich et al., ibid. and Fraedrich et al., ibid., which are incorporated herein by reference.

Factor XIII for use within the present invention may be prepared from plasma according to known methods, such as those disclosed by Cooke and Holbrook (*Biochem. J.* 141: 79–84, 1974) and Curtis and Lorand (*Methods Enzymol.* 45: 177–191, 1976), incorporated herein by reference. The $a_2$ dimer form of factor XIII may be prepared from placenta as disclosed in U.S. Pat. Nos. 3,904,751; 3,931,399; 4,597,899 and 4,285,933, incorporated herein by reference. It is preferred, however, to use recombinant factor XIII so as to avoid to the use of blood- or tissue-derived products that carry a risk of disease transmission.

Methods for preparing recombinant factor XIII are known in the art. See, for example, Davie et al., EP 268,772 and Grundmann et al., AU-A-69896/87, which are incorporated herein by reference in their entirety. Within a preferred embodiment, the factor XIII $a_2$ dimer is prepared cytoplasmically in the yeast *Saccharomyces cerevisiae* as disclosed in copending U.S. patent application Ser. No. 07/741,263, incorporated herein by reference in its entirety. The cells are harvested and lysed, and a cleared lysate is prepared. The lysate is fractionated by anion exchange chromatography at neutral to slightly alkaline pH using a column of derivatized agarose, such as DEAE Fast-Flow Sepharose™ (Pharmacia) or the like. Factor XIII is then precipitated from the column eluate by concentrating the eluate and adjusting the pH to 5.2–5.5, such as by diafiltration against ammonium succinate buffer. The precipitate is then dissolved and further purified using conventional chromatographic techniques, such as gel filtration and hydrophobic interaction chromatography.

As will be appreciated by those skilled in the art, it is preferred to use a factor XIII protein syngeneic with the patient in order to reduce the risk of inducing an immune response. Preparation and characterization of non-human factor XIII has been disclosed by Nakamura et al. (*J. Biochem.* 78: 1247–1266, 1975). The present invention encompasses the use of such factor XIII proteins within veterinary procedures.

As noted above, the methods of the present invention are particularly applicable to surgical procedures where substantial blood loss may be expected. These procedures include thoracic surgery such as open-heart surgery and, in particular, repeat cardiac surgery; and abdominal surgery, such as colonic resection and repair of liver or spleen trauma.

The following examples are offered by way of illustration, not limitation.

EXAMPLE 1

Twenty adult male rabbits with normal blood coagulation parameters are divided into two groups of ten animals each. The experimental group is given a bolus intravenous injection of 10 mg of recombinant factor XIII $a_2$ dimer (sufficient to raise the plasma factor XIII level to three-five times normal), 10 mg/ml in 25 mM glycine, 0.25 mM EDTA, 5% sucrose, pH 7.4. The control group is given an equivalent injection of vehicle alone. The animals are then anesthetized and their abdomens are surgically opened. The spleens are mobilized and placed onto preweighed gauze slings. Four standardized lacerations are made in the spleen of each animal and the following observations are made:

1. Bleeding time, estimated visually.
2. Blood loss, estimated as the difference between dry & wet gauze weights fifteen minutes post-injury.

EXAMPLE 2

A 70 kg adult male patient scheduled to undergo cardiac surgery with cardiopulmonary bypass is treated with a intravenous injection of 4 ml factor XIII in 25 mM glycine, 0.25 mM EDTA, 5% sucrose, pH 7.4 for a total dose of 25 mg. The patient is anesthetized by standard techniques using a short-acting barbiturate followed by maintenance with halothane and pancuronium. After administration of heparin and insertion of aortic and venous cannulae, bypass is instituted and surgery conducted. After removal from bypass, residual heparinization is reversed by administration of protamine sulfate. Pericardial and mediastinal drains are inserted prior to closure of the sternotomy and suction is applied. The drainage volume is monitored. Blood loss in drains and on swabs, and fall in hemoglobin are measured to determine efficacy of treatment. EXAMPLE 3

A 72 kg male patient scheduled for cardiac surgery with cardiopulmonary bypass is treated with factor XIII as in Example 2. The patient is anesthetized by standard techniques. After administration of heparin and insertion of aortic and venous cannulae, bypass is instituted with $2 \times 10^6$ KIU of aprotinin (Trasylol, Bayer) in the priming volume, and surgery conducted. After removal from bypass, residual heparinization is reversed by administration of protamine sulfate. Pericardial and mediastinal drains are inserted prior to closure of the sternotomy and suction is applied. The drainage volume is monitored.

Although certain embodiments of the invention have been described in detail for purposes of illustration, it will be readily apparent to those skilled in the art that the methods and formulations described herein may be modified without departing from the spirit and scope of the invention. Accordingly, the invention is not limited except as by the appended claims.

We claim:

1. A method of reducing perioperative blood loss in a patient undergoing surgery comprising administering to said patient an effective amount of factor XIII in a biologically compatible vehicle, wherein said factor XIII is substantially free of other blood coagulation factors and wherein said factor XIII is administered to said patient prior to or during said surgery, whereby perioperative blood loss by said patient is reduced.

2. The method of claim 1 wherein said factor XIII is administered prior to surgery as a bolus injection.

3. The method of claim 2 wherein said bolus injection of factor XIII is administered within one day prior to surgery.

4. The method of claim 1 wherein said factor XIII is administered at a dose of 0.1–1.0 mg per kg of patient weight.

5. The method of claim 1 wherein said factor XIII is administered at a dose of 0.15–0.4 mg per kg of patient weight.

6. The method of claim 1 wherein said factor XIII is factor XIII $a_2$ dimer.

7. The method of claim 1 wherein said factor XIII is recombinant factor XIII.

8. The method of claim 1 wherein said factor XIII is factor XIII zymogen.

9. The method of claim 1, further comprising administration of aprotinin to said patient.

10. The method of claim 9 wherein aprotinin is administered at a dose of $2 \times 10^6$ KIU to $8 \times 10^6$ KIU.

11. The method of claim 1 wherein said surgery is thoracic surgery.

12. A method of reducing perioperative blood loss in a patient undergoing surgery comprising administering to said patient a composition consisting essentially of factor XIII in a biologically compatible vehicle, wherein said factor XIII is administered to said patient prior to or during said surgery, whereby perioperative blood loss by said patient is reduced.

* * * * *